Figure 3:
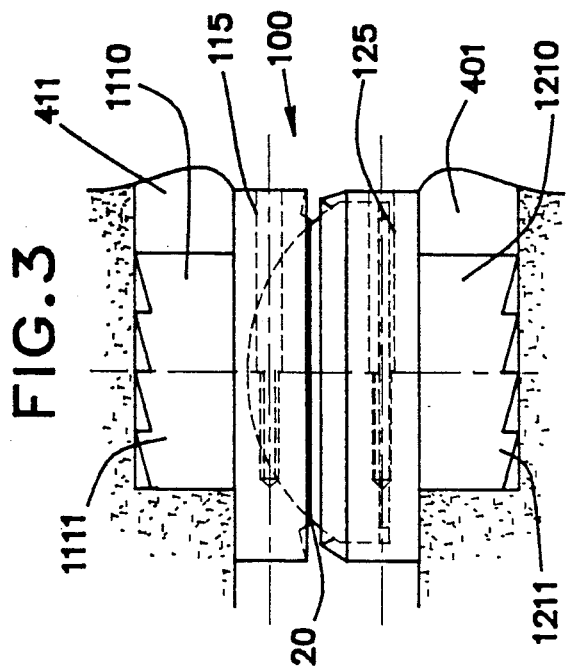

United States Patent
Marnay

[11] Patent Number: 5,314,477
[45] Date of Patent: May 24, 1994

[54] PROSTHESIS FOR INTERVERTEBRAL DISCS AND INSTRUMENTS FOR IMPLANTING IT

[75] Inventor: Thierry Marnay, Nimes, France
[73] Assignee: J.B.S. Limited Company, France
[21] Appl. No.: 773,577
[22] PCT Filed: Mar. 4, 1991
[86] PCT No.: PCT/FR91/00173
§ 371 Date: Aug. 4, 1992
§ 102(e) Date: Aug. 4, 1992
[87] PCT Pub. No.: WO91/13598
PCT Pub. Date: Sep. 19, 1991

[30] Foreign Application Priority Data
Mar. 7, 1990 [FR] France .................. 90 02997

[51] Int. Cl.⁵ .............................. A61F 2/44
[52] U.S. Cl. ............................ 623/17; 623/18; 403/112
[58] Field of Search .......... 623/17, 21, 18, 16; 606/61; 403/112, 114, 117

[56] References Cited

U.S. PATENT DOCUMENTS

| | | | |
|---|---|---|---|
| 566,360 | 8/1896 | White | 403/112 |
| 1,436,573 | 11/1922 | Choppinet et al. | 403/114 X |
| 2,836,442 | 5/1958 | Moskovitz | 403/117 |
| 3,325,197 | 6/1967 | Wehner | 403/112 X |
| 3,857,642 | 12/1974 | Miller | 403/112 X |
| 4,074,542 | 2/1978 | Hankosky et al. | 403/112 |
| 4,655,778 | 4/1987 | Koeneman | 623/21 |
| 4,756,711 | 7/1988 | Mai et al. | 623/23 |
| 4,787,908 | 11/1988 | Wyss et al. | 623/21 |
| 4,955,916 | 9/1990 | Carignan et al. | 623/21 |
| 4,997,432 | 3/1991 | Keller | 606/61 |
| 5,041,139 | 8/1991 | Branemark | 623/21 |
| 5,246,458 | 9/1993 | Graham | 623/17 |

FOREIGN PATENT DOCUMENTS

| | | | |
|---|---|---|---|
| 0042271 | 6/1981 | European Pat. Off. | |
| 0176728 | 4/1986 | European Pat. Off. | 623/17 |
| 0333990 | 9/1989 | European Pat. Off. | |
| 2263842 | 7/1974 | Fed. Rep. of Germany | |
| 3023353 | 4/1981 | Fed. Rep. of Germany | |
| 2124815 | 1/1972 | France | |
| 2372622 | 12/1976 | France | |
| 9107931 | 6/1991 | World Int. Prop. O. | 623/18 |

Primary Examiner—Randall L. Green
Assistant Examiner—D. Willse
Attorney, Agent, or Firm—Pearne, Gordon, McCoy & Granger

[57] ABSTRACT

The invention concerns a prosthesis for intervertebral discs designed to be substituted for fibrocartilaginous discs ensuring connection between the vertebrae of the spinal column and its instruments for implantation.

The prosthesis is composed mainly of two plates (110, 120) each equipped with anchoring flaps (1110, 1210) separated by a joint (20) composed of a spherical cap (21) with a cylindrical base (22), of the same diameter, made in the upper side of the lower plate (120). Each of the plates (110, 120) includes, on the back, threaded holes (115, 116, 125, 126) located parallel to the anchoring flaps (1110, 1210).

13 Claims, 6 Drawing Sheets

PROSTHESIS FOR INTERVERTEBRAL DISCS AND INSTRUMENTS FOR IMPLANTING IT

The invention concerns a prosthesis for intervertebral discs designed to replace fibrocartilaginous discs to connect the vertebra and the spinal column, and instruments for implanting it.

It is well known that the intervertebral discs often become settled, deformed, shifted or just simply wear out. The result is multiple pathological symptoms causing intense pain and some anxiety to the patients.

For a long time, the only ways surgeons could intervene, mainly to relieve the patients' pain, was simple ablation of the defective disc or intervertebral synostosis, which temporarily relieved the patient, but at times gave him/her a certain functional handicap. Over the last twenty years, recourse has been made, more or less successfully, to prostheses designed to replace intervertebral discs that were totally or partially ablated.

The research in this area has taken two routes; one is to replace the defective disc with a kneecap-type disc made of a ductile, incompressible material, placed between two corresponding plates with spherical impressions, as is described in French patent 2.372.622; the other consists of replacing the defective disc with an artificial disc made of a composite material with practically the same mechanical characteristics as the natural disc, as is described in French patent 2.124.815, namely a disc made of an elastomer reinforced with a textile material.

A combination of these two research routes produced a prosthesis, as described in the application for European patent 0.042.271, whose main goal is a two-part prosthesis that has a hemispheric pad and a hemispheric impression, respectively; one part is metal and the other synthetic (polyethylene, polymethacrylate).

While these disc prostheses make it easy to restore and maintain over time a normal separation between the vertebrae (7 to 14 mm), keeping them in a transverse position leaves something to be desired, for the relative movement of the vertebrae concerned causes progressive misalignment of the prosthesis, causing pathological symptoms requiring fast surgical intervention. To attempt to solve this problem, certain disc prostheses have been equipped, on the outside of the pressure plates, with small clamps designed to be implanted in each of the vertebra as soon as the surgeon releases the separating force initially applied in order to separate the vertebra sufficiently so that the prosthesis may be put into position. However, this lateral joining method is effective only when the vertebra remain parallel and, consequently, when the spinal column is not subject to flexure. It is easy to see that this cannot happen in the opposite case, for then the clamps remain supported in their impressions on the side of the flexure, while they escape from the opposite side; which causes gradual staggering of the impressions when the flexure is accompanied by a certain rotation. Consequently, the prosthesis gradually moves away from its ideal location and is ultimately expelled, causing serious problems.

Furthermore, it is difficult to reconcile, in terms of the kneecap, the characteristics of flexibility and incompressibility, which are often accompanied by a certain sensitivity to wear and to creep; which has thus far caused certain manufacturers of prostheses for intervertebral discs to resort to three-part units, permitting the introduction of a dual kneecap joint composed of two spherical caps with large radii, opposite the base. However, this concept, although it allows the contact surfaces in particular to be increased, has the disadvantage of substantially reducing the thickness of the dual kneecap joint and making it easier to dislocate it, by ejection, particularly when the spinal column flexes near the vertebrae concerned, since this attraction is translated into a pinching of the dual kneecap joint in the direction of the flexure, accentuating the separation in the other direction.

The purpose of this invention is to remove these disadvantages. This invention, as it is characterized, solves the problem of creating an intervertebral disc prosthesis with which, on the one hand, the thrust of the upper vertebra on the lower vertebra is transmitted, whatever the relative inclination of the two vertebrae, through elements with a large supporting surface that offer good resistance to wear and give the unit a certain flexibility while controlling the relative longitudinal and transverse angular clearance of the vertebrae concerned. The upper and lower parts of the prosthesis are well enough anchored in their respective vertebral plates to prevent any risk of their coming apart; and this is done without making the vertebrae fragile and using simple instruments which are easy to use.

The intervertebral disc prosthesis in the invention is mainly characterized by the fact that it is composed of two plates, each equipped with anchoring flaps, separated by a joint piece consisting of a spherical cap with a cylindrical base, implanted with force in a cylindrical cavity with the same diameter in the upper side of the lower plate, and by the fact that each of the plates has in the back threaded holes placed symmetrically on both sides of the cylindrical cavity and parallel to the anchoring flaps.

The angular clearance of the upper and lower plates, in relation to one another, is limited to a value alpha by two two-step flanges, with complementary sections, located respectively on the circumference of the upper plate and the circumference of the lower plate.

The two-step flange on the lower plate takes up the whole part located between the edge of the implantation cavity of the joint and the edge of said plate, while the two-step flange in the upper plate takes up the whole part located between the edge of the semispherical cavity ensuring the range of the joint and the edge of said plate.

The diameter (D) of the semicylindrical cavity, which ensures the range of the joint, and the geometric characteristics of the two-step flanges, upper and lower, are determined so that, when said flanges overlap one another, the maximum relative angular pitch alpha of the plates corresponds to that which exists naturally between two vertebra, namely around 15°.

The two steps of the upper plate are composed of the junction of an annular surface, inclined toward the base of said plate at an angle beta of around 10° from its edge, and another annular surface from the edge of the semispherical cavity forming an angle delta of around 70° in relation to the base of the plate.

The two-step flange of the lower plate is composed of the junction of an annular surface, raised at an angle theta of around 20° C. in relation to the base of said plate, and of another annular surface going from the edge of the cylindrical cavity, forming an angle gamma of around 60° C. in relation to the base of the plate.

According to one preferred embodiment, the base of the joint is supported, in the bottom of its implantation cavity by a washer, made of a flexible material, with a diameter (d) less than that (D) of the joint; said joint is made of polyethylene, the plates are made of titanium or titanium alloy, and their surfaces in contact with the vertebrae are pretreated with plasma to facilitate osteosynthesis.

The anchoring flaps of the plates in the base of the vertebrae are tapered and have, on their ends, a "sawtoothed" relief, and the upper edge of the teeth is inclined toward the front in the direction in which the flaps are introduced into their mortises.

The width (l) of the mortises is a little less than the thickness (E) of the flaps, measured at their base.

The instruments for implanting the prosthesis in the invention are characterized by the fact that they are composed mainly of:

a set of vertebra alignment and mortise gauges,
an osteotomy chisel to produce the mortises,
a prosthesis impact tip, with a built-in shock-absorbing plate
a tool for maneuvering the gauges, prosthesis impacters and osteomy chisel,
a clamp for positioning the prosthesis,
a prosthesis extractor.

The alignment and mortise gauges are composed of a plate of an appropriate thickness, with the same shape and space requirements as the corresponding plates of the prosthesis, which has rounded angles rear the front and a threaded dummy hole from back to front the same size as the threaded end of the gauge and impacter rod, located in the median longitudinal plane of the plate, and four grooves, two opposite the other two, symmetrically placed on either side of the median longitudinal plane of the plate at a distance that corresponds exactly to the distance separating the anchoring flaps from each of the plates. The length of the grooves is determined so as to limit the penetration of the osteomy chisel to a depth just sufficient for anchoring and precisely positioning each of the plates. Said chisel has a heel limiting its longitudinal penetration to a depth corresponding to the length of the grooves.

The prosthesis impacter tip is composed of a threaded element, shaped like a parallelepiped, made of a soft material, one end of which opposite the threads conforms to the form of the prosthesis and the other end of which is equipped with a shock-absorbing plate made of a hard material.

The tool for maneuvering the gauges, the prosthesis impact tip and the osteomy chisel is composed mainly of a metal rod, one end of which is threaded to the size of the threaded hole of the groove gauges, the impact tip and the heel of the osteomy chisel, and the other end of which has a driving square preceded by a semicircular throat on which a retractable sleeve is fitted by means of a tappet, which is pushed to the outside by a spring for locking and unlocking with a mobile cylindrical key in an oblong housing. The locking and unlocking are done by two tangential grooves of different depths made in the tappet.

The prosthesis positioning pliers are composed of handles, normally kept apart by a spring, each equipped with a tip molding the shape of the plates of the prosthesis, including two rods designed to penetrate to the inside of the holes provided in the plates for that purpose.

The prosthesis extractor is composed of four parallel rods, with a knurled maneuvering knob and threaded end mounted to slide in a collective maneuvering plate, which also serves as a mounting gauge on the threaded end of the rods in the threaded holes of the plates of the prosthesis and an impact body for disassembly.

The advantages obtained from the invention basically consist of the fact that the prosthesis is constantly kept in its ideal position, with no risk of displacement or premature dislocation due to the anchoring of each of the plates by two flaps which immobilize it from turning and a crosspiece by increasing the surface in contact with the bone and preventing posterior expulsion, since the mortises do not cross the posterior cortical of the vertebra, and preventing anterior expulsion since the flaps have teeth of an appropriate shape on their ends that are implanted in the bottom of the grooves, and also because of the fact that there is a certain osteosynthesis with the metal of the plates (titanium), enhanced by the plasma pretreatment, because of the limitation of movement to around 15° by the two-step flanges forming stops and because of the method of implantation of the joint in the lower plate.

This prosthesis is implanted using simple means that do not permit false interpretation or malpractice in making the anchoring mortises and positioning the plates.

Figure 1:
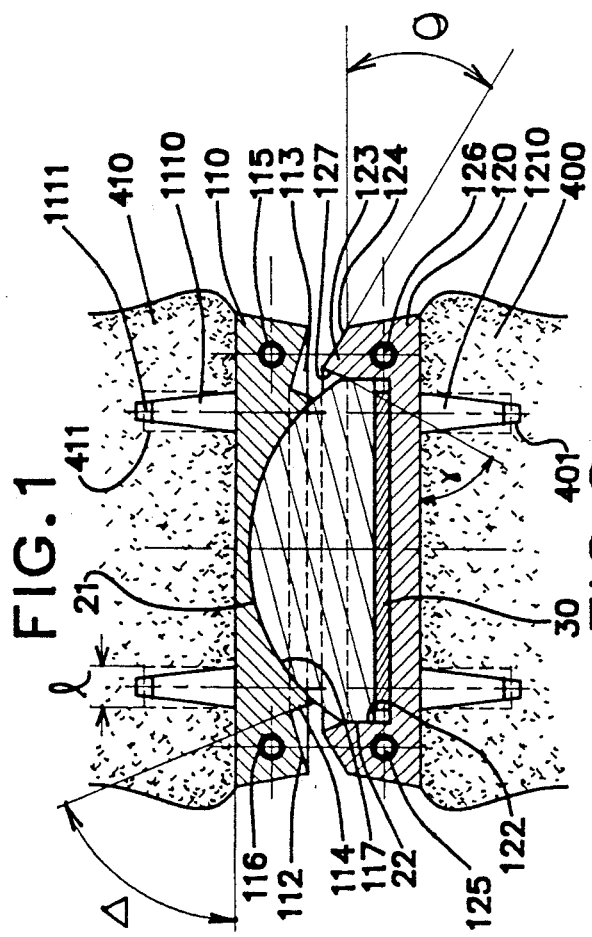
Figure 2:
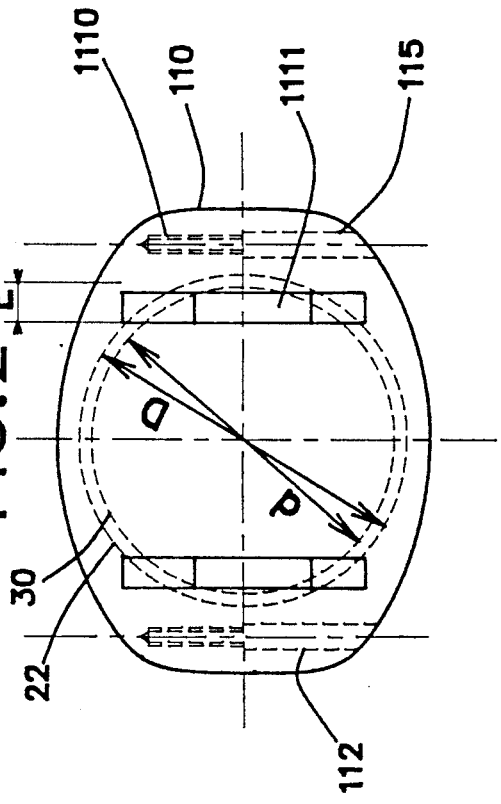
Figure 4:
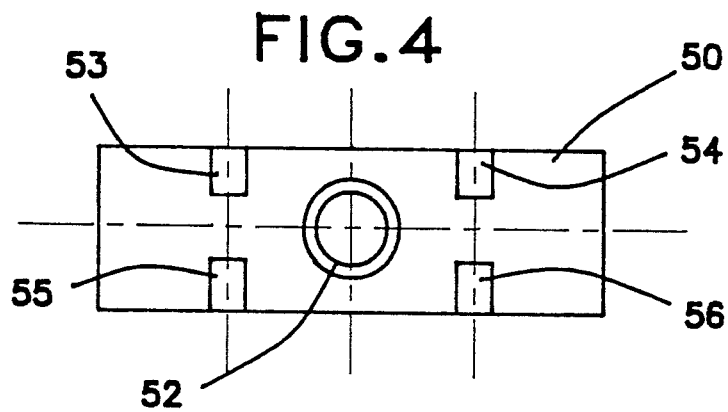
Figure 5:
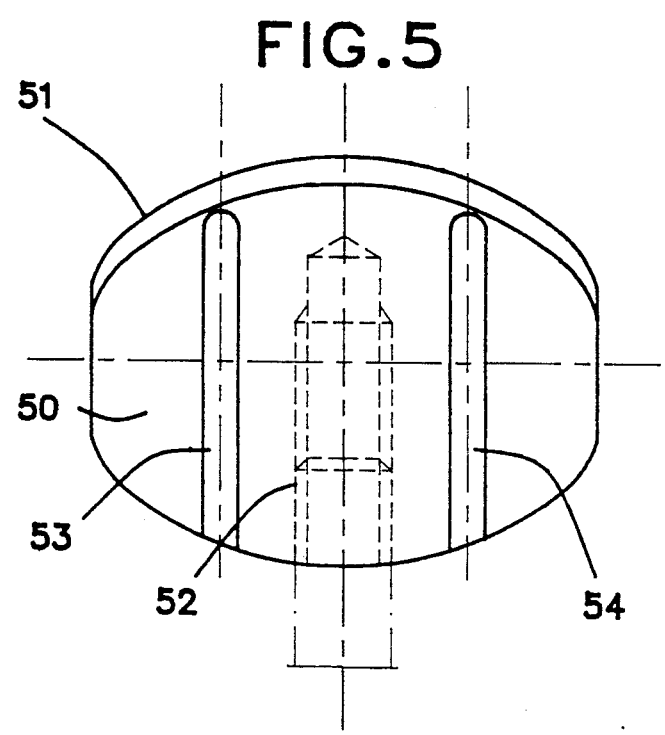

Other characteristics and advantages will appear in the following description of a prosthesis for intervertebral discs and instruments for positioning it made according to the invention, which are given as nonlimiting examples with reference to the appended drawings, in which:

FIG. 1 shows a frontal view, in longitudinal section, of the prosthesis, in place between two vertebrae shown in partial section, FIG. 2 shows a view of the prosthesis from above, FIG. 3 shows a side view of the prosthesis, in place between two vertebrae shown in partial section, FIG. 4 shows a front view of a gauge for mounting and mortising, FIG. 5 shows an overview of a gauge for mounting and mortising in place at the end of the rod of the maneuvering tool (broken line)

Figure 6:
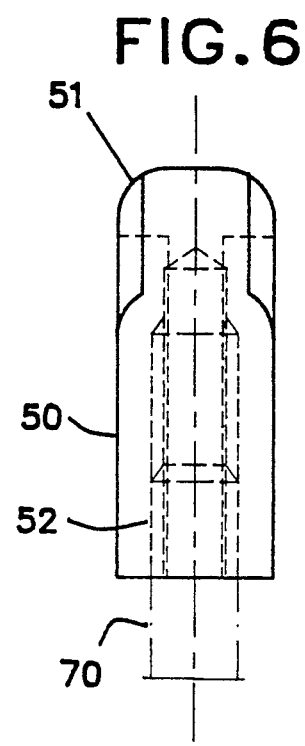

FIG. 6 shows a side view of a gauge for mounting and mortising in place at the end of the rod of the maneuvering tool (broken line)

Figure 7:
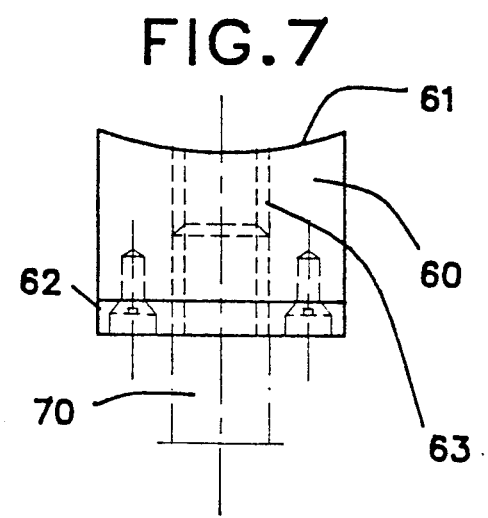
Figure 8:
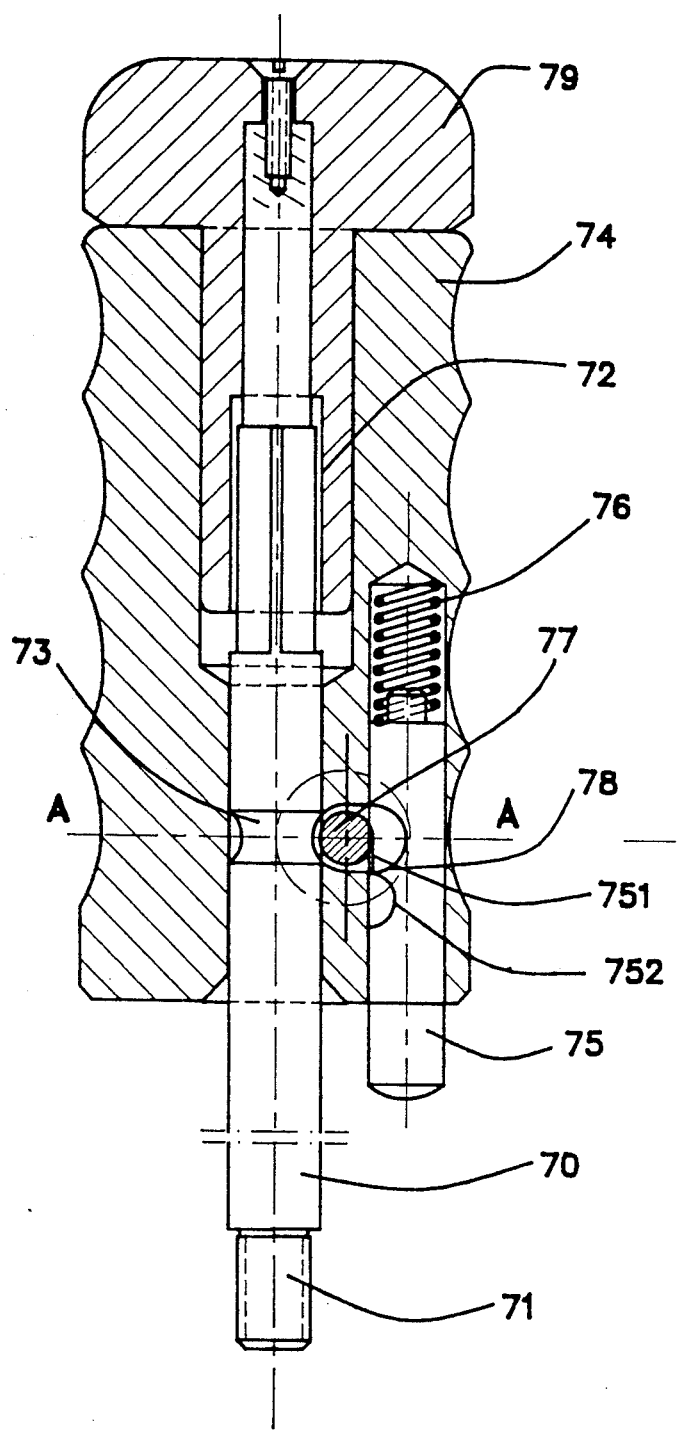
Figure 9:
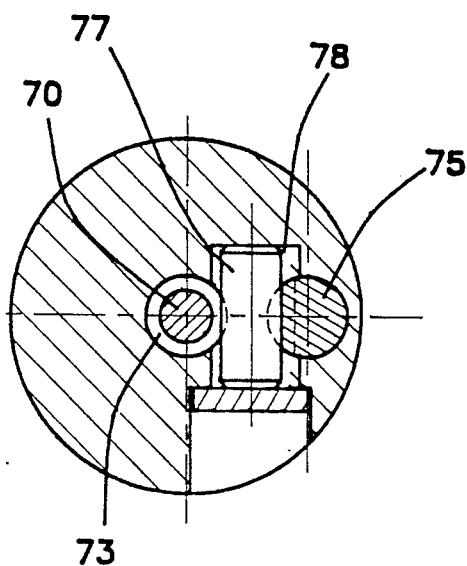
Figure 10:
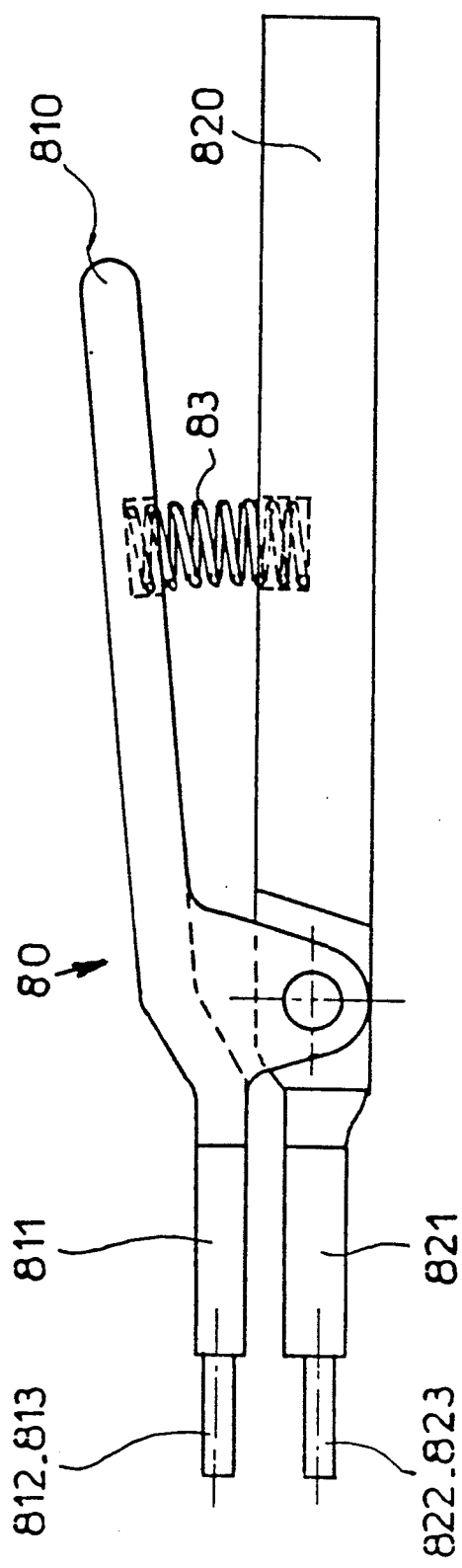
Figure 11:
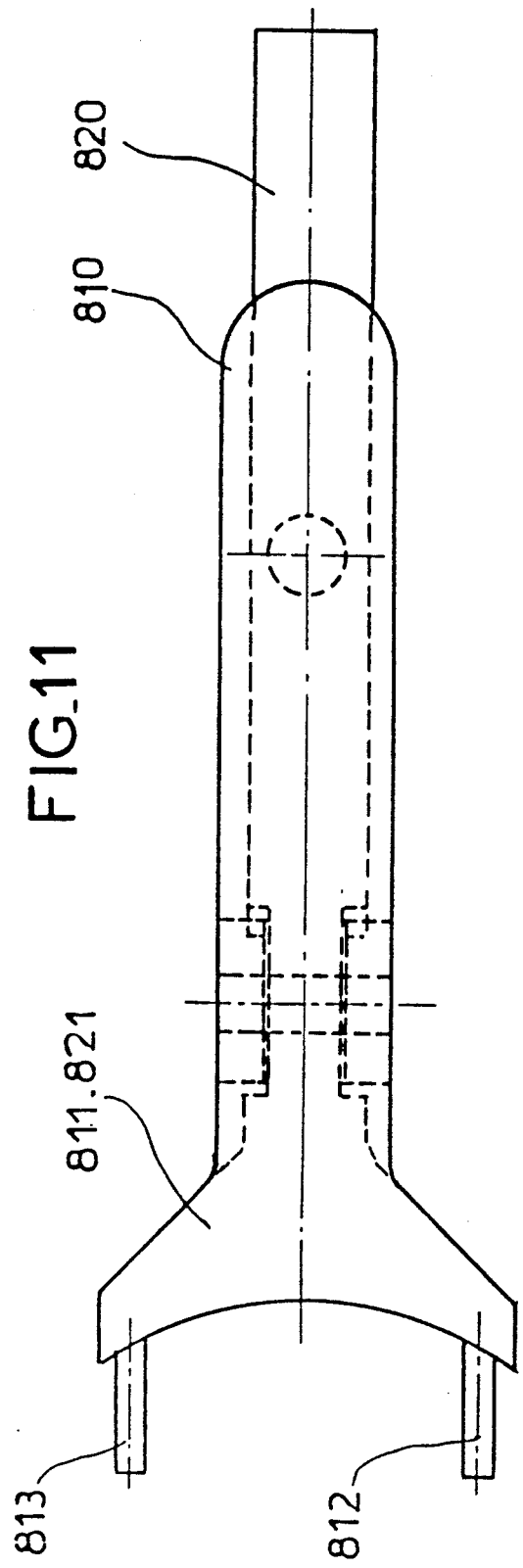
Figure 12:
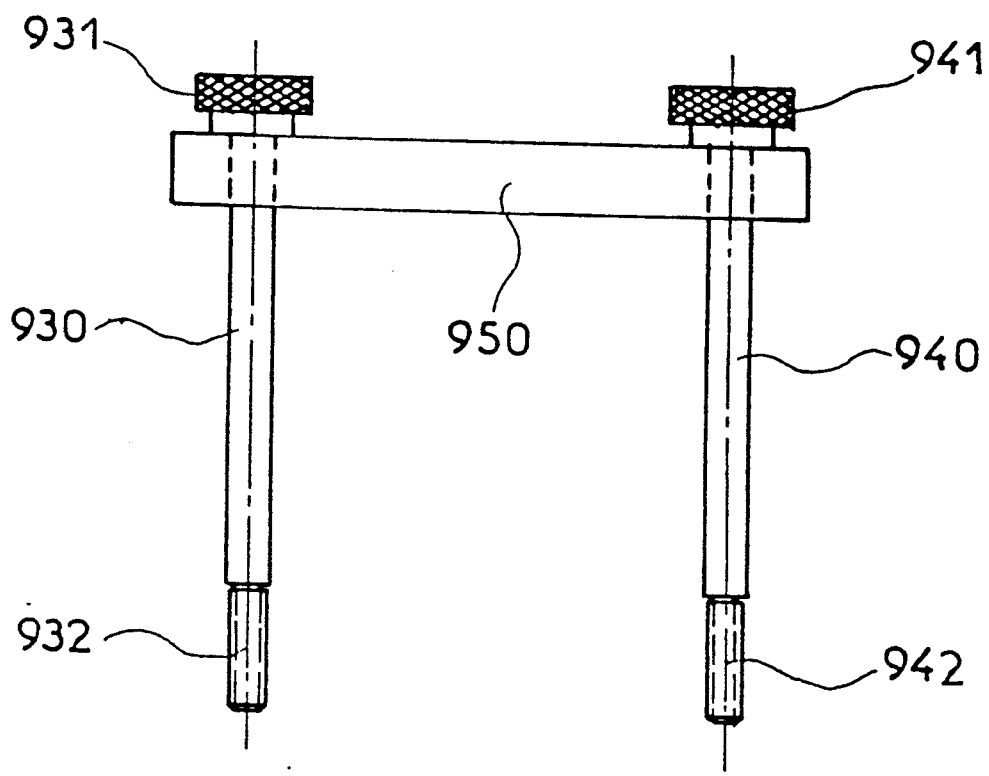
Figure 13:
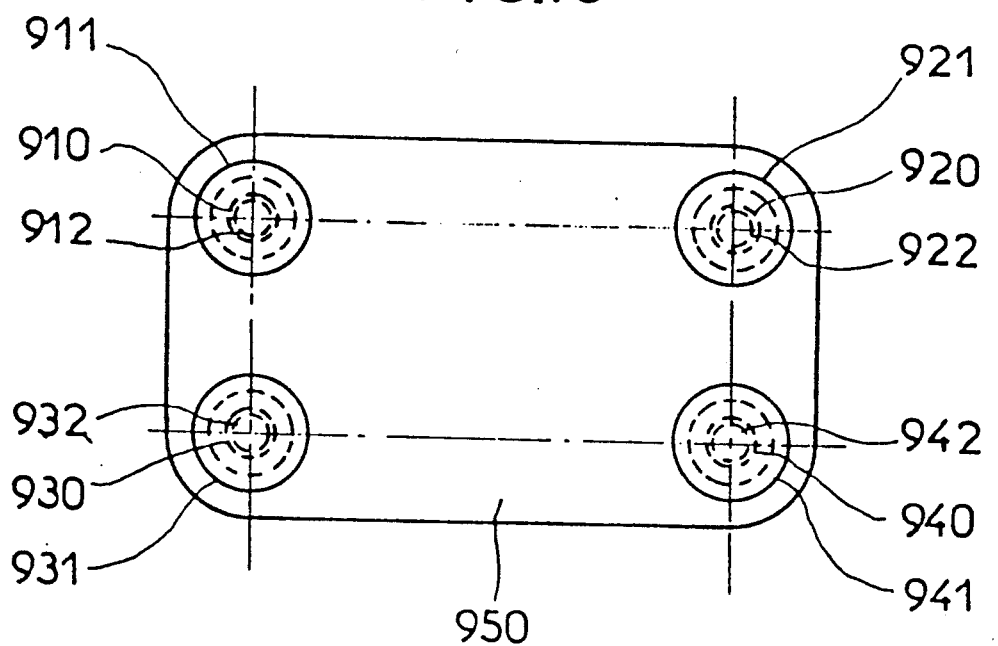
Figure 14:
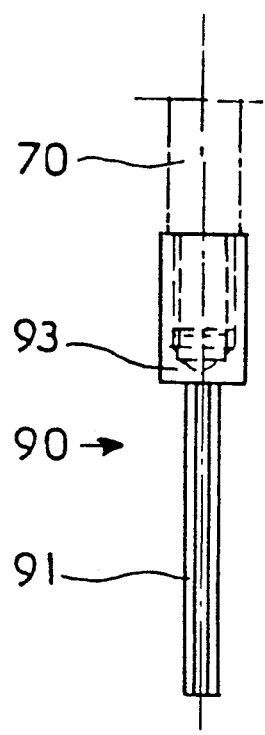
Figure 15:
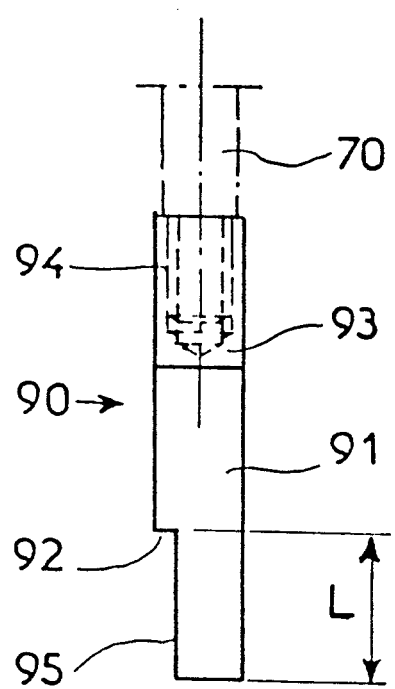
Figure 16:
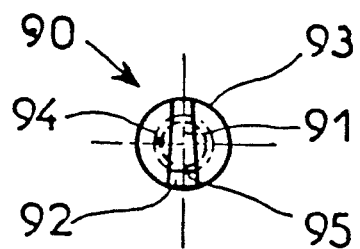

FIG. 7 shows a front view of a prosthesis impact tip, in place at the end of the rod of the maneuvering tool (broken line), FIG. 8 shows a view of a longitudinal section of the maneuvering tool, FIG. 9 shows an overview of the maneuvering tool, in section according to the plane AA, FIG. 10 shows a side view of the prosthesis positioning pliers, FIG. 11 shows an overview of the pliers for positioning the prosthesis, FIG. 12 shows an overview of the prosthesis extractor, FIG. 13 shows a front view of the prosthesis extractor, FIG. 14 shows an overview of the osteotomy chisel, FIG. 15 shows a side view of the osteotomy chisel, FIG. 16 shows a front view of the osteomy chisel.

FIGS. 1 to 3 show a prosthesis 100 for intervertebral discs 400 and 410 that basically includes two plates 110 and 120, each equipped with anchoring flaps 1110, 1210, separated by a joint 20 composed of a spherical cap 21 with a cylindrical base 22, implanted in a cylindrical cavity 122 with the same diameter (D) made in the upper side of the lower plate 120, with an interposed flexible washer 30 with a diameter (d); said plates 110, 120 have threaded holes 115, 116 and 125, 126 located symmetrically on both sides of the cylindrical cavity 122 and two-step flanges 113 and 123, with complementary sections, composed respectively of the junction of an indented annular surface 112, inclined at an angle beta of around 10° from the edge, and another annular surface 114, from the edge of the semispherical cavity 117, inclined at an angle delta of around 70° in relation to the base of the upper plate 110, and the junction of an annular surface 124 raised at an angle theta of around 20° in relation to the base of the lower plate 120, and another annular surface 127, from the edge of the cylindrical cavity 122 forming an angle gamma of around 60° in relation to the base of the lower plate 120. The anchoring flaps 1110 and 1210 are threaded and have a "sawtoothed" relief 1111 and 1211 on their ends; the teeth are inclined toward the front in the direction in which they are introduced into the mortises 401 and 411 made beforehand using osteotomy chisel 90 in the vertebrae 400, 410 using a gauge 50 which will now be described.

The alignment and mortising gauges 50 according to the invention shown in FIGS. 4 and 6, forming a set of different dimensions, are composed of a plate of the same thickness, the same shape and the same spatial requirements as the plates 110 and 120 of the prosthesis 100, and have rounded angles 51 near the front and, from back to front, a threaded dummy hole 52 designed to permit joining to the threaded end 71 of the rod 70 of the positioning tool. Said gauges have four grooves 53, 54, 55, 56 separated by a distance corresponding to the distance separating the anchoring flaps 1110 and 1210 from the plates 110 and 120; the length of the grooves 53, 54, 55 and 56 is determined so as to limit the penetration of the osteotomy chisel 90 to a depth just sufficient for precisely anchoring each of the plates 110, 120; the blade 91 of said chisel 90 has a heel 92 limiting its penetration to the length of the grooves 53, 54, 55, 56, whose end must correspond largely to the posterior cortical of the vertebrae.

The prosthesis impacter tip 60 according to the invention shown in FIG. 7 is composed mainly of an element in the shape of a parallelepiped, made of a soft material, one end of which 61 conforms to the form of the outside edge of the plates 110, 120, and the other end of which is equipped with a threaded hole 62 allowing the end 71 of the rod 70 of the tool to be screwed in, and includes a shock-absorbing plate 63 made of a hard material.

The tool for maneuvering the gauges 50, the prosthesis impacter tip 60 and the osteotomy chisel 90, shown in FIGS. 8 and 9, is mainly composed of a metal rod 70, the end of which (71) is threaded to the dimensions of the threaded holes 52 and 62, gauges 50 and impact tip 60.

The other end of this rod has a driving square 72 for the sleeve 74, which is adapted at will on the rod by means of the semicircular throat 73 made on the rod, under the driving square 72, and a mobile cylindrical key 77 in an oblong housing 78 arranged in the sleeve 74; said key 77 can be pushed back to the outside by a spring 76 activated by a button 75, locked in the bottom of the throat 73 of the rod, or entirely released from it, depending on whether or not pressure has been applied in the axis of said button 75; impressions of different depths 751 and 752 may be made tangentially to the button 75 to do this. The sleeve 74 has a metal shock part 79 on its upper part for applying shocks directly to the rod 70 on its axis.

The prosthesis positioning pliers 80, shown in FIGS. 10 and 11 are composed of two handles 810 and 820, normally kept apart by a spring 83, the ends of which each have a tip 811, 821 molding the shape of the plates 110, 120 of the prosthesis and including two rods 812, 813 and 822, 823 designed to penetrate to the inside of holes 115, 116 and 125, 126 made for that purpose in the plates. Said holes are consequently threaded only part way down from the bottom; this threaded length is only used upon withdrawal, along with the extractor which will be described now.

This prosthesis extractor 900, shown in FIGS. 12 and 13 is composed of four rods 910, 920, 930, 940, one end of which 912, 922, 932 and 942 is threaded to the size of the threaded holes in the prosthesis and the other end of which has knurled buttons 911, 921, 931, 941 mounted to slide in a plate 950 forming a crosspiece and a shock body.

Looking now at FIGS. 14, 15 and 16, one can see that the osteotomy chisel 90 is composed mainly of a base 93 with a threaded hole 94 the size of the threaded end 71 of the rod 70 of the maneuvering tool, extended by a blade 91 with a heel limiting its penetration 92. The blade 91 is threaded toward the side opposite the heel 92. The length (L) of the back 95 of the active part of the blade is a little thinner (E) than the flaps 1110, 1210, measured at their base; this is so that there can be clamping after installation in the mortises 401, 411 made by using the gauge 50 and the osteotomy chisel 90.

The process for using the prosthesis implantation instruments for intervertebral discs according to the invention consists of performing the following operations in order:

eliminating the defective intervertebral disc using the usual methods and instruments, separating the vertebrae to permit insertion of a gauge 50 chosen on the basis of the particular features of the vertebrae concerned 400, 410, making the mortises 401, 411 designed to permit anchoring of the plates 110, 120 in the vertebrae 400, 410 by means of the flaps 1110, 1210. This mortising is done with the osteotomy chisel 90, which has been screwed on the threaded end 71 of the rod of the maneuvering tool for this purpose; said chisel is inserted successively in the grooves 53, 54, 55 and 56, introducing its blade 91, with its back 95 against the bottom of said grooves, so that the threaded part is pointed toward the vertebra 400 or 410 concerned and the heel 92 of the blade is opposed to penetration of it beyond the length strictly necessary for implantation of the anchoring flaps 1110, 1210. This length has been determined so that the flaps come to a stop against the posterior cortical of the vertebra, so as to eliminate any risk of posterior expulsion of the prosthesis, withdrawing the gauge 50, after all the upper and lower mortises have been made, while keeping the vertebrae 400, 410 separated to permit insertion of the prosthesis 100, positioning the prosthesis 100 between the vertebrae 400, 410 using the positioning pliers 80, the four rods of which 812, 813 and 822, 823 have been previously introduced into the holes 115, 116 and 125, 126 of the prosthesis plates 110 and 120. Complete insertion of the flaps 1110, 1210 into their mortises is facilitated by exerting pressure, or impact at the end of one of the handles 820 of the pliers, which have been extended and formed for this by placing the end 821 with the rods 822, 823 in the extension of said handle 820, releasing the separation effort, exerted on the vertebrae 400, 410 to obtain total support of the joint 20 in the semispherical cavity 117 of the upper plate 110, of the upper and lower plate 110 and 120 against the vertebrae 400, 410 and the end of the teeth 1111 of the flaps 1110 and 1210 against the bottom of the mortises 401 and 411; which, taking into account the shape of the teeth, eliminates any risk of anterior expulsion of the prosthesis.

Certain circumstances may require that the prosthesis be extracted and replaced; this may be done by proceeding as follows:

separate the vertebrae 400, 410 using a regular separator so as to eliminate the pressure exerted on the prosthesis and to make it easier to loosen its plates 110, 120, mount the prosthesis extractor 900 by screwing the threaded ends of the rods 910, 920, 930 and 940 after putting them in the holes provided for that purpose in the connecting plate 950, in the threaded holes 115, 116, 125, 126 in the plates 110 and 120 of the prosthesis 100, so as to be able, by exerting shock under the knurled buttons 911, 921, 931 and 941 by means of the plate 950, to loosen the plates and disengage the flaps 1110, 1210 from their mortises 401, 411, the replacement prosthesis will be put into place by proceeding as indicated above for inserting the original prosthesis.

The prosthesis for intervertebral discs and its implantation instruments according to the invention are designed mainly for vertebral surgery.

I claim:

1. An intervertebral disc prosthesis for placement in a lateral direction between vertebrae, each vertebra having a pair of mortises cut into the vertebra in the lateral direction, said prosthesis comprising:
    a cap having a convex bearing surface and an opposite mounting surface;
    a first plate having a vertebra-contacting surface and an opposite cap-retaining surface including a cavity receiving said cap mounting surface in a fixed orientation with respect to said first plate; and
    a second plate having a vertebra-contacting surface and an opposite concave bearing surface, said bearing surfaces cooperating to provide a pivoting joint between said plates, said vertebra-contacting surfaces each having a pair of anchoring flaps extending from said vertebra-contacting surface toward respective vertebra, said flaps being sized to engage said mortises when said prosthesis is inserted between said vertebrae in said lateral direction.

2. A prosthesis according to claim 1, characterized by the fact that the angular clearance of the first (120) and the second (110) plates, one in relation to the other, is limited by two-step flanges (113, 123), with complementary sections, located respectively on the periphery of the second plate (110) and on the periphery of the first plate (120).

3. A prosthesis according to claim 2, characterized by the fact that the two-step flange (123) placed in the first plate (120) extends from the periphery of said cavity to the periphery of said plate (120).

4. A prosthesis according to claim 2, characterized by the fact that the two-step flange (113) in the second plate (110) extends from the periphery of said concave bearing surface to the periphery of said second plate (110).

5. A prosthesis according to claim 4, characterized by the fact that the cavity is cylindrical and that the diameter of the cylindrical cavity (122) and the geometric characteristics of the two-step flanges (113) (123) are determined so that when said flanges (112, 123) overlap, the maximum relative angular staggering of the plates (110, 120) corresponds to that which exists naturally between two vertebrae.

6. A prosthesis according to claim 3, characterized by the fact that the two-step flange (113) of the second plate (110) is composed of the junction of an annular surface (112) inclined toward the vertebra-contacting surface of said second plate (110) at an angle of around 10° from the periphery of said annular surface, and another annular surface (114) from the periphery of said concave bearing surface forming an angle of around 70° in relation to the vertebra-contacting surface of the second plate (110).

7. A prosthesis according to claim 4, characterized by the fact that the two-step flange (123) of the first plate (120) is composed of the junction of an annular surface (124) raised at an angle of around 20° in relation to the vertebra-contacting surface of said first plate (120), and another annular surface (127) from the periphery of the cylindrical cavity (122) forming an angle of around 60° in relation to the vertebra-contacting surface of the first plate (120).

8. A prosthesis according to claim 1, characterized by the fact that the cavity is cylindrical, the cap mounting surface is flat and circular and that the cap mounting surface (22) is supported in the bottom of the cylindrical cavity by a circular washer, made of a flexible material (30) with a diameter less than that of the cap mounting surface (22).

9. A prosthesis according to claim 1, characterized by the fact that the anchoring flaps (1110, 1210) of the plates (110, 120) have a toothed extremity (1111, 1211).

10. A prosthesis according to claim 9, characterized by the fact that each tooth of the toothed extremities has an inclined edge oriented to resist movement opposite to the direction in which the flaps are placed into said mortises (401, 411).

11. A prosthesis according to claim 1, characterized by the fact the flaps (1110, 1210) have a thickness near the vertebra-contacting surfaces that is somewhat greater than the width of the respective mortises.

12. A prosthesis according to claim 1, characterized by the fact that the plates (110, 120) and flaps (1110, 1210) are made of titanium, or titanium alloy, plasma treated on all surfaces coming into contact with the vertebrae.

13. A prosthesis according to claim 1, characterized by the fact that the cap is made of polyethylene.

* * * * *